United States Patent
Salvetti et al.

(10) Patent No.: US 7,914,201 B2
(45) Date of Patent: Mar. 29, 2011

(54) LOW COST MULTIMODE CALORIMETER

(75) Inventors: Giuseppe Salvetti, San Giuliano Terme (IT); Elpidio Tombari, San Giuliano Terme (IT); Carlo Ferrari, Pisa (IT); Luciano Lepori, Pappiana San Giuliano Terme (IT); Roberto Ambrosetti, Pisa (IT); Domenico Ricci, Ronchi (IT); Alessandro Barbini, San Giuliano Terme (IT); Luca Gasperini, Pisa (IT); Maria Rosaria Tine, Pisa (IT); Luca Bernazzani, Grosseto (IT); Enrico Matteoli, Pisa (IT); Fabio Papucci, Cascina (IT)

(73) Assignee: CNR Consiglio Nazionale Delle Richerche, Rome (IT)

( * ) Notice: Subject to any disclaimer, the term of this patent is extended or adjusted under 35 U.S.C. 154(b) by 514 days.

(21) Appl. No.: 11/815,776

(22) PCT Filed: Feb. 22, 2006

(86) PCT No.: PCT/IB2006/000371
§ 371 (c)(1),
(2), (4) Date: Jan. 9, 2008

(87) PCT Pub. No.: WO2006/090247
PCT Pub. Date: Aug. 31, 2006

(65) Prior Publication Data
US 2008/0247441 A1    Oct. 9, 2008

(30) Foreign Application Priority Data
Feb. 22, 2005 (IT) .............................. PI2005A0020

(51) Int. Cl.
*G01K 17/00*    (2006.01)
(52) U.S. Cl. ........ 374/34; 374/31; 374/33; 374/E17.001
(58) Field of Classification Search .................... 374/31, 374/33, 34, E17.001
See application file for complete search history.

(56) References Cited

U.S. PATENT DOCUMENTS 3,718,437 A * 2/1973 Paloniemi .................. 374/33

(Continued)

FOREIGN PATENT DOCUMENTS

WO    WO 9618886 A1  *  6/1996

(Continued)

OTHER PUBLICATIONS

Wessel et al. "Purity Determination of Organic Compounds by Adiabatic Calorimety" Euromet Purity Workshop Paris NMI-The Art of Measurement, Nov. 21, 2003, pp. 1-18.*

(Continued)

*Primary Examiner* — Lisa M Caputo
*Assistant Examiner* — Jonathan Dunlap
(74) *Attorney, Agent, or Firm* — Dennison, Schultz & MacDonald (57) ABSTRACT

A structure of calorimeter provides a calorimetric head (1) comprising a calorimetric cell (10) suitable for receiving a sample holding container (20) containing a sample (25) to examine. The cell (10) is arranged according to a first shield (3), or active shield. Outside the active shield (3) a second shield (4), or dynamical shield is present, which comprises a cylindrical hollow body arranged around the active shield (3) for all its length in order to provide a space (5) of determined size. Outside the active shield a thermal bath is present (not shown) at a temperature lower than the first and the second shield (3,4). The dynamic shield (4) allows an effective adjustment of the heat flux through the active shield (3) during calorimetric measures by limiting the heat flux same. In fact, in operative conditions the dynamic shield acts as thermal flywheel and keeps constant the heat flux coming from the active shield (3). More in detail, the presence of the dynamic shield (4) ensures the reduction of the temperature gradient on the active shield (3) and then on the cell (10) containing the sample (20). Furthermore, by keeping the dynamic shield (4) at a suitable temperature difference from the active shield (3), the temperature can be controlled with much less electric power than it would be necessary if the active shield (3) exchanged heat directly with the thermal bath.

13 Claims, 5 Drawing Sheets

U.S. PATENT DOCUMENTS 4,892,707 A * 1/1990 Stockton et al. ................. 374/33
4,963,499 A * 10/1990 Stockton et al. ................. 374/33

FOREIGN PATENT DOCUMENTS

WO        WO 9960356 A1 * 11/1999

OTHER PUBLICATIONS

Barbini et al. "Differential Microcalorimeter for Liquid Samples" Review of Scientific Instruments, vol. 60, No. 7, Part 1. Jul. 1, 1989. pp. 1308-1311.*

* cited by examiner

LOW COST MULTIMODE CALORIMETER

FIELD OF THE INVENTION

The present invention relates to a structure of calorimeter for measuring thermodynamic quantities of a sample, in particular the heat capacity and the heat developed or adsorbed by chemical reactions and physical transformations.

Furthermore, the invention relates to a method that uses this structure of calorimeter for controlling heat flux and thermal gradient in different calorimetric modes.

BACKGROUND OF THE INVENTION

As well known, for carrying out precise thermodynamic measurements of physical quantities, such as the heat capacity of bodies or materials, or the heat developed from chemical reactions, it is necessary to provide calorimeters having good sensitivity, precision, adaptation to the characteristics of the sample, as well as the possibility of inspecting wide temperature ranges. In particular, calorimeters of good quality can be used for controlling industrial processes and for investigating products as long as they are easy and can be arranged within in automatic measuring procedures.

An example of calorimeter with thermal bath is described as MASC, i.e. "Modulated Adiabatic and Scanning Calorimeter", in Italian patent application PI 98A000044 and in some scientific articles (G. Salvetti, et al. "A Modulated Adiabatic Scanning Calorimeter (MASC).", Thermochemical Acta, 364, 11-22 (2000); C. Cardelli, et al. "n-Dodecane melting studied with the combined use of different calorimetric modes.", Thermochemical Acta, 364, 1-10 (2000)].

It comprises, in particular a head having a cylindrical body of aluminium with a central hole into which a calorimetric cell is put. The function carried out by this particular configuration of calorimetric head is that of creating an environment at uniform temperature and radial heat exchanges around the calorimetric cell. Furthermore, the MASC has further advantages among which the main are the following: the capacity of a multi-mode operation with a same cell, the possibility of describing with precision the cell-sample system with a calculation model using the measured physical quantities, simultaneously measuring the complex heat capacity and the enthalpy of the process, controlling and minimizing the temperature gradient on the sample in all the operative range.

However, the MASC above described and other calorimeters of prior art have some drawbacks. In particular, the delicacy of the measurement and analysis procedures, which often requires qualified operators, and the low adaptation typical of calorimeters available on the market, notwithstanding many possible applications, are the main obstacles against spreading of calorimetry.

SUMMARY OF THE INVENTION

It is therefore a first feature of the invention to provide a structure of calorimeter capable of a high steadiness of response time and a higher sensitivity with respect to the prior art.

It is another feature of the invention to provide a structure of calorimeter having a high mechanical strength capable of assuring a long life and a safer use to the instrument.

It is a further feature of the invention to provide a structure of calorimeter structurally easy and cheap with respect to the calorimeters of prior art.

It is also a feature of the invention to provide a structure of calorimeter of simple structure and that can be used for industrial applications of different fields such as the production of pharmaceuticals, alimentary-agricultural stuff, plastic materials, resins and paints, as well as for research and education activities.

These and other features are accomplished with one exemplary structure of a calorimeter, according to the present invention, for carrying out thermodynamic measurements on a sample, said structure comprising:
  a calorimetric head having:
    a calorimetric cell in which the sample is inserted,
    a temperature sensor suitable for measuring the temperature of the calorimetric cell;
    means for heating the calorimetric cell,
    a first shield, or active shield, arranged around the cell,
    a temperature sensor suitable for measuring the temperature of the first shield;
    means for heating the first shield,
  a thermal bath located at a reference temperature substantially less than the temperature of the calorimetric head,
  an electronic control unit for setting the heat flux delivered by the heating means the cell and the first shield responsive to temperature signals determined by the temperature sensors, said control unit being suitable for keeping the cell and the first shield at a determined temperature difference,
whose main feature is that the calorimetric head comprises, furthermore:
  at least a second hollow shield, or dynamical shield, arranged around the first shield in order to define with it a determined volume, the second shield being adapted to limit the heat flux from the first shield towards the thermal bath.

In particular, in operative conditions the second shield acts from thermal flywheel and keeps constant the heat flux coming from the first shield. More in detail, the presence of the second shield ensures the reduction of the temperature gradient on the first shield and then on the cell containing the sample. Furthermore, by keeping the second shield at a suitable temperature difference with respect to the first shield, the temperature can be controlled with much less electrical power than would be necessary if the first shield exchanged heat directly with the thermal bath.

Advantageously, the calorimetric head comprises furthermore:
  means for heating the second shield,
  a temperature sensor suitable for measuring the temperature of the second shield,
  a control unit for setting the heat flux delivered between the first shield and the second shield by the heating means responsive to temperature signals determined by the temperature sensors, said control unit being suitable for keeping the first and the second shield at a determined temperature difference.

In particular, the first and the second shield of the calorimetric head have tubular shape, are arranged coaxially and centred axially.

Advantageously, the calorimetric cell, in which the sample holding container for the tested sample is inserted, provides a introduction/extraction duct that crosses the calorimetric head at least for a part thereof. In particular, the duct and the first shield are separated by a gap.

Preferably, the introduction/extraction duct has a high length/diameter ratio so that the radial heat flux is slight with respect to the axial heat flux.

Advantageously, at a determined position the duct has a stop element, for example a narrow passage, for holding the sample.

Preferably, the introduction/extraction duct crosses the first and the second shield for all its length and comprises a central portion made of a material with high thermal conductivity, for example copper, and two side portions made of a material with lower thermal conductivity.

In particular, the duct is arranged according to the first shield in such a way that the central portion is centred axially with respect to the first shield.

Advantageously, the calorimetric head has pneumatic sealing elements, such as o-rings, sealing materials, etc.

In particular, the sealing elements can be arranged only at the gap between the first shield and the duct.

Alternatively, pneumatic sealing elements are provided also at the end of the second shield, at the outlet of the duct, etc., in order to keep in sealing conditions all the calorimetric head. The pneumatic sealing conditions thus obtained, which ensure in particular the absence of humidity in the calorimetric head, ensure also the repeatability of the heat exchange coefficient between cell and active shield, $\lambda(T)$ and then the reproducibility of the measurement.

In the gap between the duct and the first shield and/or in the space between the first and the second shield a gas can be inserted, for example air dehumidified.

In particular, means can be provided for introducing/extracting the sample holding container into/away from the calorimetric cell, such as at least one arm operated by an pneumatic or hydraulic actuator.

Advantageously, the means for extracting comprise at least one gas jet, in particular of air.

Furthermore, means can be provided for adjusting the temperature of the thermal bath, such as a fan, where the temperature of the bath is kept at the room temperature, or alternatively, a coil exchanger cooling system for applications at temperatures below zero Celsius degrees.

According to another aspect of the invention a method for controlling the heat flux for calorimetric measures on a sample comprises the steps of:

arranging the sample in a calorimetric cell,
arranging a first shield out of the calorimetric cell,
arranging a second shield out of the first shield in order to define a determined volume between them,
heating the first shield and monitoring this heating for keeping the first shield at a determined temperature,
arranging about the second shield a thermal bath at known temperature in any case less than the temperature of the first shield,
measuring the temperature of the cell,
controlling the heat flux between the cell and the first shield by controlling the temperature of the cell and the temperature of the first shield.

In particular, the first shield is kept at a temperature equal to the cell, whereby the heat flux between the cell and the first shield is zeroed.

Advantageously, further steps are provided of heating the second shield and monitoring this heating for keeping the second shield at a temperature lower than the first shield for a determined value, whereby the heat flux towards/away from the first shield is constant.

BRIEF DESCRIPTION OF THE DRAWINGS

The invention will now shown with the following description of an exemplary embodiment thereof, exemplifying but not limitative, with reference to the attached drawings wherein.

DESCRIPTION OF A PREFERRED EXEMPLARY EMBODIMENT

Figures 1, 2, 3:
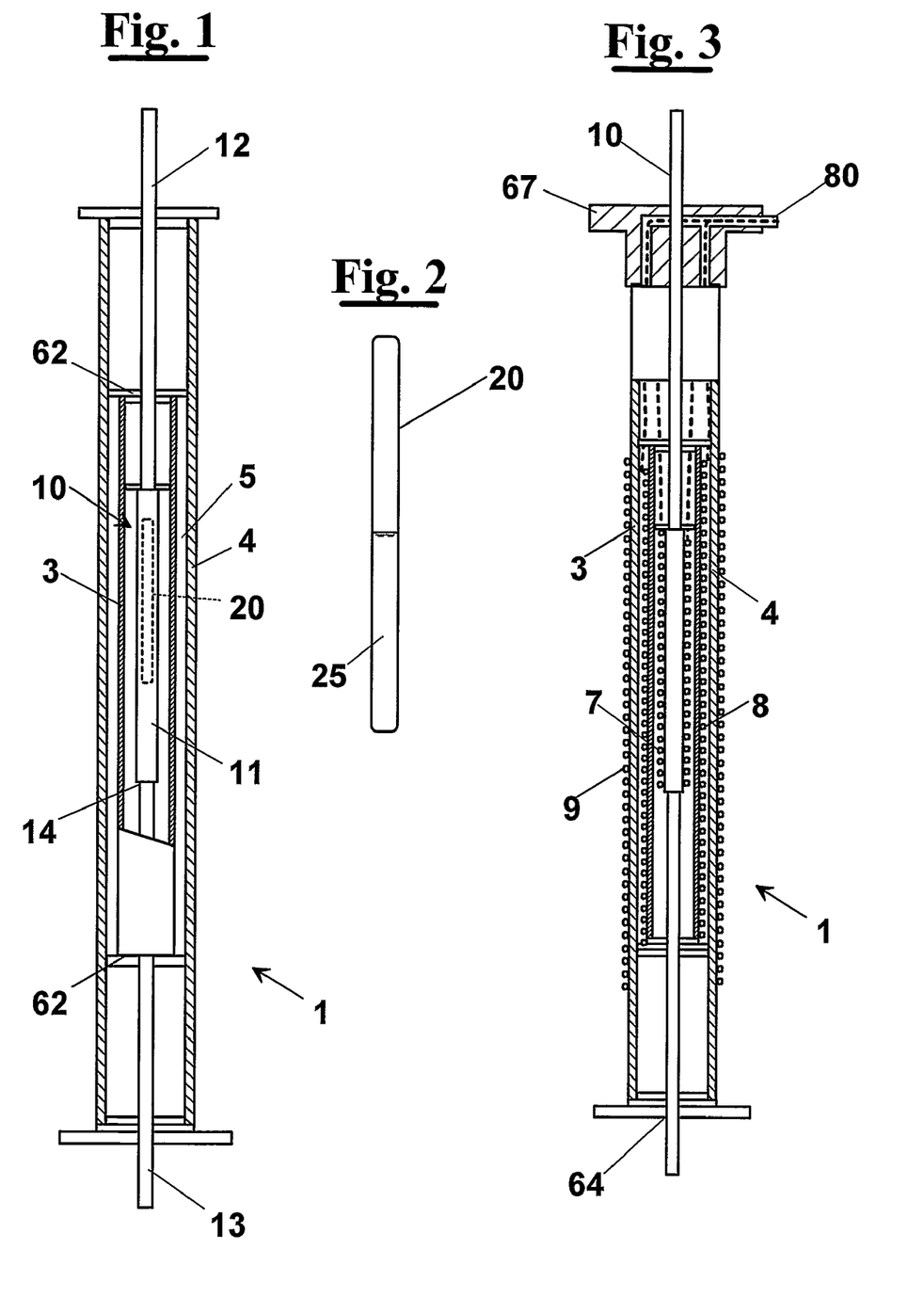
FIG. 1 shows diagrammatically an elevational front view of a calorimetric head used in the structure of calorimeter, according to the invention.
FIG. 2 shows diagrammatically an elevational front view of a first exemplary embodiment of a sample holding container for a sample to examine.
FIG. 3 shows diagrammatically an elevational front view of a first exemplary embodiment of the calorimetric head of FIG. 1.

With reference to FIG. 1, a structure of calorimeter according to the invention provides a calorimetric head 1 comprising essentially a calorimetric cell 10 suitable for receiving a sample holding container 20, containing a sample 25 to examine. Cell 10 is arranged within a first shield 3, hereafter called active shield. Outside active shield 3 a second shield 4 is present, hereafter called dynamical shield, which comprises a cylindrical hollow body arranged around active shield 3 for all its length, in order to provide a space 5 of determined size.

Sample holding container 20 can be a cylindrical tube, made for example of Pyrex glass or other material adapted to chemical and/or physical processes, shown in FIG. 2 in a way enlarged with respect to the cell of FIG. 1. Sample holding container 20 can be let down from the above into cell 10, for example by a wire.

Figure 7:
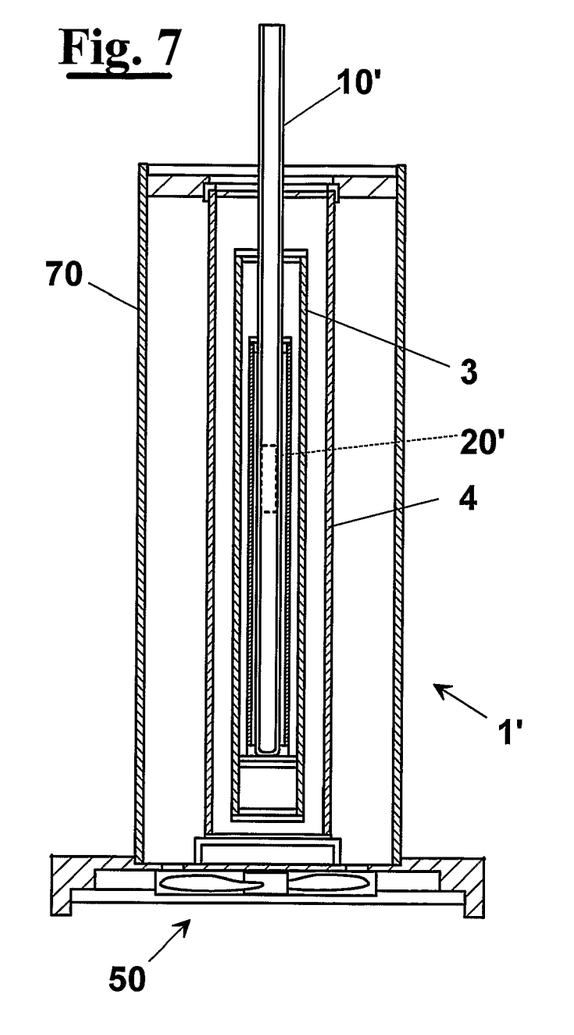
FIG. 7 shows diagrammatically an elevational front view of a further exemplary embodiment of the head of FIG. 1 arranged in a thermal bath.
Figure 8:
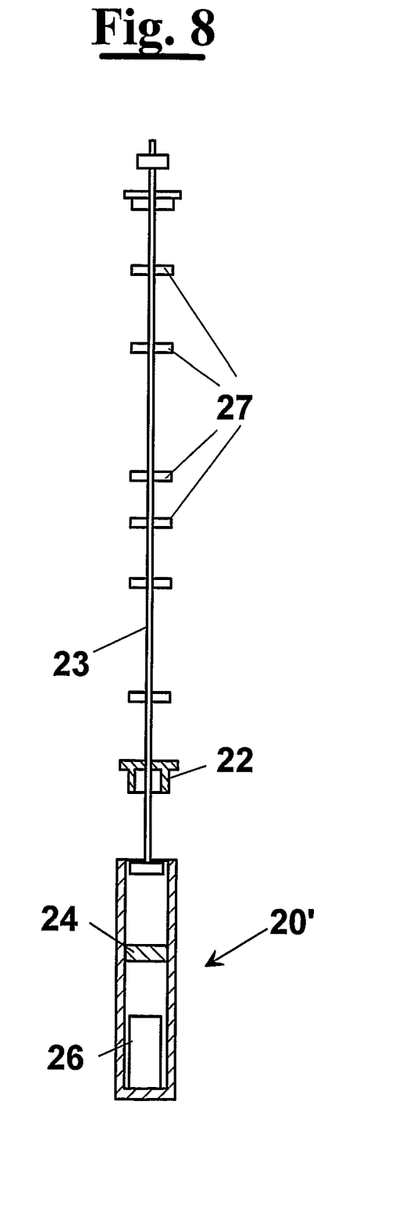
FIG. 8 shows diagrammatically an elevational front view of an exemplary embodiment of the sample holding container of FIG. 2.

An alternative configuration of the sample holding container is diagrammatically shown in FIG. 8 with 20', in combination with calorimeter 1' of FIG. 7. It provides substantially a blind duct 21, closed by a tight stopper 22 (shown in open position). Sample holding container 20' can be split into two distinct volumes by a diaphragm 24, that can be broken to bring into contact either two liquids or a solid 26 and a liquid not shown. It can provide concentric capillary tubes 23 of stainless steel that allow: a flow of a liquid into duct 21, an air outflow, an introduction of a conductive wire and/or a rod for breaking the diaphragm 24 and/or a stirring operation of the sample mixture manually or with a suitable stirrer. Around the capillary tubes 23 discs 27 can be arranged for guiding the introduction from the above of sample holding container 20' into cell 10' of calorimeter 1'.

With reference again to FIG. 1, in particular, dynamic shield 4 allows an effective adjustment of the heat flux, by limiting the heat fluxes through active shield 3 during calorimetric measures. In fact, the dynamic shield acts as thermal flywheel and in operative conditions it keeps constant the heat flux coming from active shield 3. More in detail, the presence of dynamic shield 4 ensures the reduction of the temperature gradient on active shield 3 and then on cell 10 that contains sample 20. Furthermore, by keeping dynamic shield 4 at a suitable temperature difference from active shield 3, the temperature can be controlled with much less electric power than it would be necessary if active shield 3 directly exchanged heat with the thermal bath.

Calorimetric cell 10 can be formed within a through duct 12, i.e. a duct crossing calorimetric head 1 for all its length (FIGS. 1, 3 and 4), or alternatively, can be formed in a duct put into calorimetric head 1 only for a part thereof (FIG. 7), according to the applications of the calorimeter. In particular, duct 10 of FIG. 1 has a high length/diameter ratio so that the axial heat flux is slight with respect to radial heat flux. More in detail, it provides three portions 11-13 of different material, and precisely a central portion 11, which is the actual calorimetric cell, made of a material with high thermal conductivity, for example copper, suitable for reducing the axial temperature gradient, and two side portions 12 and 13 of a material with lower thermal conductivity, for example stainless steel. At the end of central portion 11 elements are provided for blocking sample holding container 20, such as a narrow passage 14, suitable for allowing the arrangement of the sample holding container and to ensure that it remains at a determined position.

During the tests, the thermodynamic parameters on sample 25, its temperature and the temperature of first active shield 3, are instantly detected by means of temperature sensors in order to adjust the heat flux by means of heaters.

In particular, the temperature sensors and the heaters can be, for example, resistors 7 and 8 (FIG. 3), which are arranged on the central portion 11 of duct 10 and at least on one part of active shield 3, and in particular are wound on each of them, in an uniform anti-inductive way, i.e. two adjacent coils at fixed pitch. For example, each resistor 7, or 8, can comprise as heater an electrically insulated wire of manganine (alloy comprising 70-80% Cu, 15-25% Mg, 2-5% Ni characterized by having almost fixed resistivity in a wide temperature range), and as temperature sensor a wire of a Nickel alloy, also electrically insulated. The winding step of the wires of manganine and of Nickel alloy is preceded by the deposition of a thick film of electrically insulating material, which is also resistant at the maximum temperature of operation, arranged on portion 11 of cell 10 and on active shield 3. The wound wires are, then, connected mechanically with a second insulating film, which coats them.

As shown in the preferred exemplary embodiment of FIG. 3, also shield 4 can be controlled by means of temperature sensors and its temperature can be adjusted by means of heaters operatively connected to it, for example by means of resistors 9 of the type described above for active shield 3 and cell 10.

Figures 4, 5, 6:
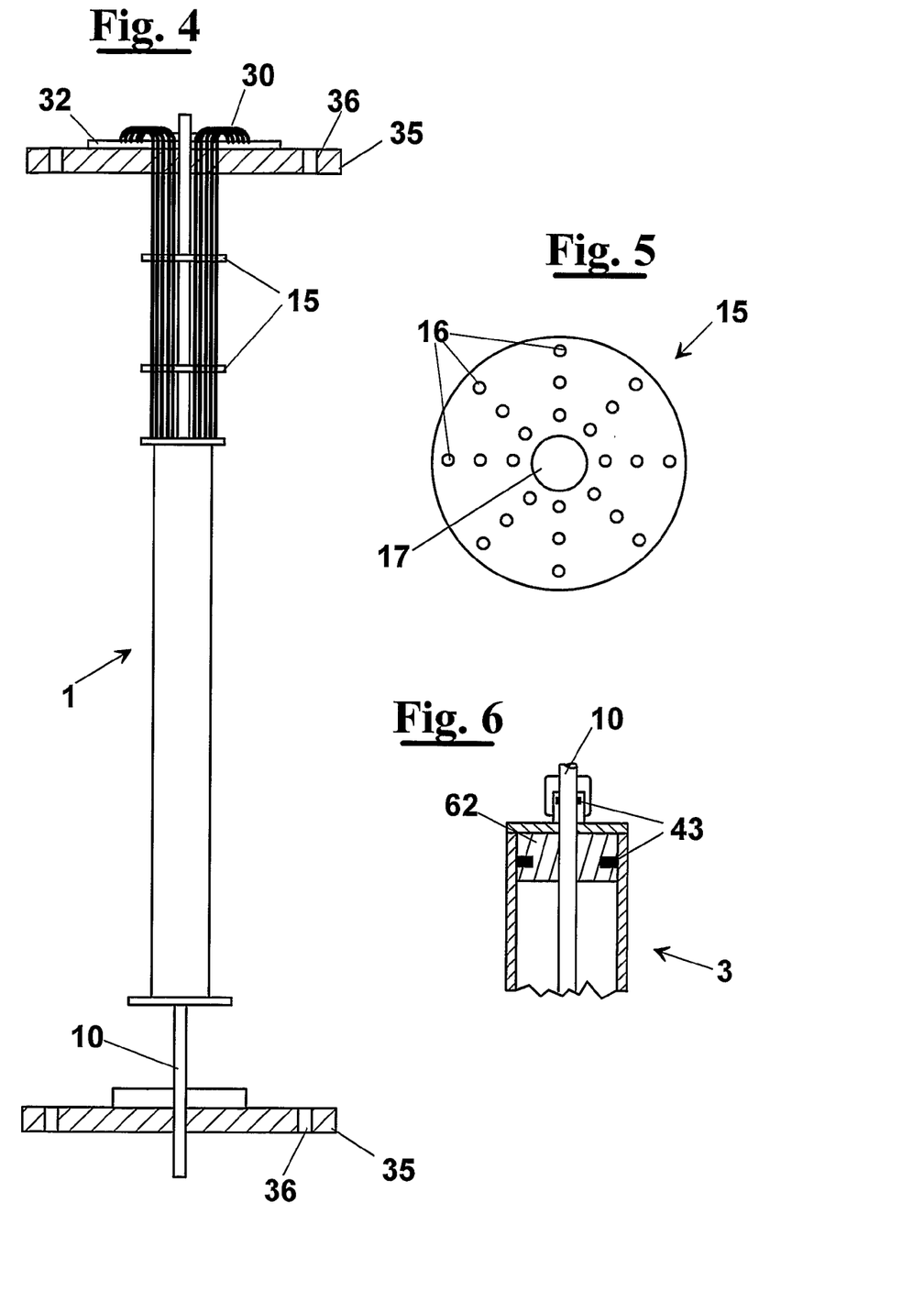
FIG. 4 shows diagrammatically an elevational front view of the support frame of the calorimetric head of FIG. 1 with the electric connections of the temperature sensors, heaters and connection flange with the container for the thermal bath.
FIG. 5 shows in detail a top plan view of an element of the frame of FIG. 4.
FIG. 6 shows in detail a partially cross sectioned view of an element of the calorimetric head of FIG. 1.

The ends of the resistors 7, 8 and 9 respectively associated to cell 10, to active shield 3 and to dynamic shield 4, are welded on discs of metal coated Vetronite (epoxy glass) 32. The electric connection between the different elements of the structure of calorimeter is effected by means of wires 30 of manganine, for example having a 100 micron diameter and low thermal conductivity. Wires 30 are kept distinct and stretched by discs of insulating material 15 connected along duct 10 at regular distance and have holes 16 distributed along concentric circumferences (FIGS. 4 and 5). The spacing among wires 30 allows, in particular to obtain a high and steady with time electric insulation. The wires 30 of manganine have ends out of calorimetric head 1, where they meet electric connections for the resistance measurements and for programmable suppliers.

The first shield 3, or active shield, and the second shield 4, or dynamical shield, may have cylindrical shape and may be made of copper, or other material with high thermal conductivity. More in detail, active shield 3, dynamic shield 4 and cell 10 can be assembled in order to result centred both in a axial direction that in a radial direction.

Figure 9:
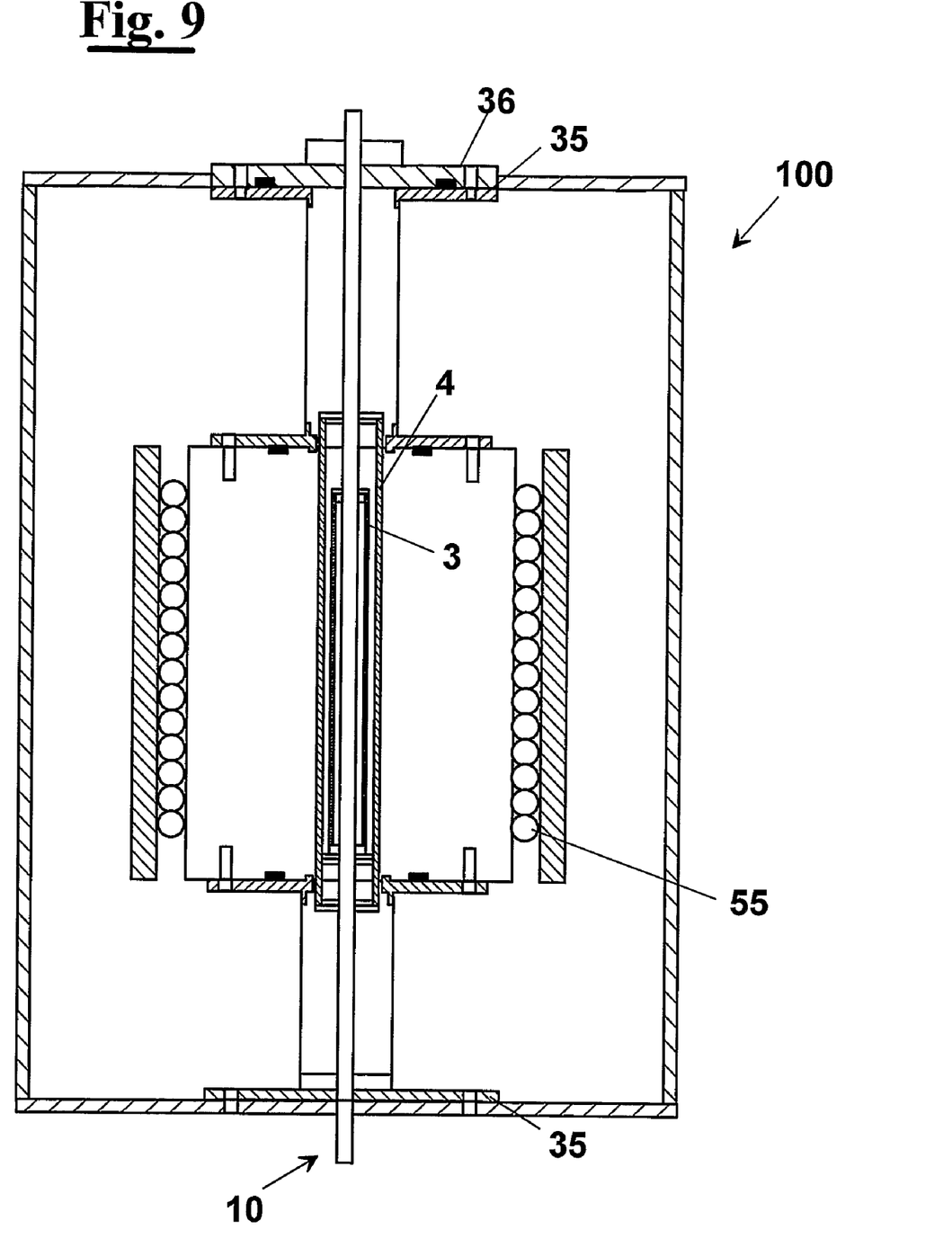
FIG. 9 shows diagrammatically an, elevational front view of the calorimetric head of FIG. 1 arranged in a thermal bath.

Calorimetric head 1, in operative conditions, is arranged in a container 100 (FIG. 9) for a thermal bath, which is set at a reference temperature substantially less than the temperature of head 1. In particular, head 1 is connected to container 70 by means of flanges 35 integral to container 100.

The temperature of the thermal bath can be adjusted by a air fan 50 (FIG. 7) in case of processes carried out at a temperature higher than the environment, or alternatively, by means of a cooling coil exchanger 55 (FIG. 9) in case of processes carried out at a temperature lower than the environment. In this case, it can be advantageously used a Peltier cooler for processes carried out at a temperature higher than −20° C., whereas cooling groups with expander by a cylindrical propeller are preferred in case of processes carried out at a temperature higher than −40° C.

Figure 10:
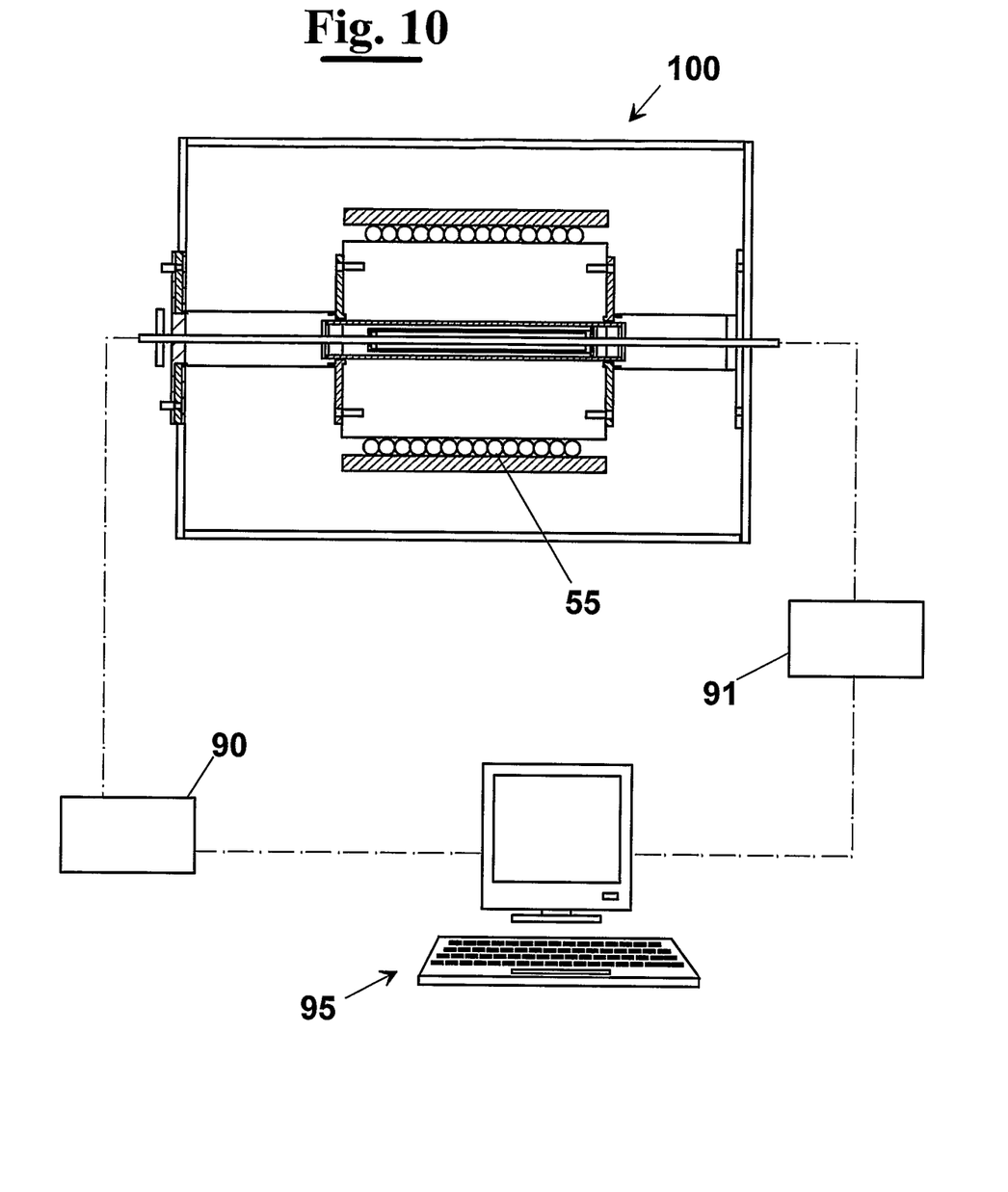
FIG. 10 shows diagrammatically, finally, a possible layout for the structure of calorimeter, according to the invention, along with its control means.

The control of the temperature data coming from the sensors and the adjustment of the power supplied by the heaters, to keep predetermined process conditions, are made through the control unit diagrammatically shown in FIG. 10. They comprise: analog-digital converters for converting the analog data measured by the temperature sensors into digital data, a PC 95 to which the temperature data are sent for being computed by a determined software, and programmable voltage suppliers 90 operated by PC 95 in order to provide the predetermined temperature variation on the central part 11 of cell 10 and on shields 3 and 4.

More in detail, when scanning the control unit keeps shield 4 at a predetermined temperature difference, for example 5° C., with respect to active shield 3, keeping the heat flux between the two shields constant.

To ensure, the pneumatic sealing conditions in calorimetric head 1, and, in particular the absence of humidity inside, and then to ensure the repeatability of the heat exchange coefficient $\lambda(T)$ between cell 10 and active shield 3, calorimetric head 1 has pneumatic sealing elements. These may be high temperature sealing materials, or O-rings 43 (FIG. 6), located at stoppers 62 of active shield 3. In this case, the O-rings 43 carry out also the function of keeping cell 10 and active shield 3 (FIG. 6) co-axial to each other.

A possible alternative embodiment, also advantageous for time and costs of production, is presented in FIG. 3. In this case, the sealed zone is not only the gap between cell 10 and active shield 3, but all calorimetric head 1. Therefore, stoppers 62 at the end of active shield 3 do not have O-rings and have the function of easy centering means of active shield 3 on duct 10. The tightness on wires 30 is effected by a bi-component glue, such as Torr-Seal glue produced by Varian, adapted for high vacuum conditions at the end 64 of shield 4, at the outlet of duct 10 by stopper 64, which blocks calorimetric head 1 on the side of the electric connections. Duct 80 is made at the stopper 67 of head 1, for connecting the sealed volume with the outside. The tightness between side portions 12 of duct 10, shield 4 and stopper 67 is obtained with normal welding. In this configuration, in the calorimetric head the vacuum can be made through the duct 80 and then a suitable gas inserted, typically dry air, in a easy and controlled way.

The calorimetric head according to the invention can be used for industrial applications of many industrial fields, but also for research and education. For example, the exemplary embodiments of FIGS. 1 and 3 can be more suitable for industrial applications, whereas the exemplary embodiment of FIGS. 7 and 8 can be more suitable for research and education.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. A calorimeter for carrying out thermodynamic measurements on a sample comprising:
   a calorimetric head having:
     a calorimetric cell in which the sample is inserted,
     a temperature sensor suitable for measuring the temperature of the calorimetric cell;
     means for heating the calorimetric cell,
     a first shield, or active shield, arranged around the cell,
     a temperature sensor suitable for measuring the temperature of the first shield;
     means for heating the first shield,
   a thermal bath constructed and arranged to be held at a reference temperature substantially less than the temperature of the calorimetric head,
   an electronic control unit for setting heat flux delivered by the heating means to the cell and the first shield responsive to temperature signals determined by the temperature sensors, said control unit being suitable for keeping the cell and the first shield at a determined temperature difference, and
   at least a second hollow shield, or dynamical shield, arranged around the first shield in order to define therewith a determined volume, the second shield being adapted to limit the heat flux from the first shield towards the thermal bath,
   wherein said calorimetric cell provides an introduction/extraction duct that crosses said calorimetric head at least for a part thereof, said duct and said first shield being separated by a gap, and
   wherein said introduction/extraction duct crosses said first and said second shield for all its length and comprises a central portion made of a material with high thermal conductivity and two side portions made of a material with lower thermal conductivity.

2. The calorimer according to claim 1, additionally comprising:
   means for heating said second shield,
   at least one temperature sensor suitable for measuring the temperature of said second shield,
   a second control unit for setting the heat flux delivered between said first and said second shield by said means for heating responsive to temperature signals determined by said temperature sensors, said control unit being suitable for keeping said first and said second shield at a determined temperature difference.

3. The calorimeter according to claim 1, wherein said first and said second shield have a tubular shape, are arranged coaxially and are centred axially.

4. The calorimeter according to claim 1, wherein said introduction/extraction duct has a high length/diameter ratio, whereby axial heat flux is slight with respect radial heat flux.

5. The calorimeter according to claim 1, wherein at a determined position said duct has a stop element for holding the sample.

6. The calorimeter according to claim 1, wherein said duct is arranged according to said first shield in such a way that said central portion is centred axially with respect to said first shield.

7. The calorimeter according to claim 1, wherein said calorimetric head has pneumatic sealing elements.

8. The calorimter according to claim 1, wherein in said space between said first and second shield and/or in the gap between said first shield and said duct a dry gas is present.

9. The calorimeter according to claim 1, additionally comprising means for introducing/extracting said sample holding container into/away from said duct.

10. The calorimter according to claim 1, additionally comprising means for adjusting the temperature of said thermal bath.

11. Method for controlling the heat flux for calorimetric measures on a sample, comprising the steps of:
    arranging said sample in a calorimetric cell,
    arranging a first shield out of said calorimetric cell,
    arranging a second shield out of said first shield in order to define a determined volume between them,
    heating said first shield and monitoring this heating for keeping said first shield to a determined temperature,
    arranging about said second shield a thermal bath at known temperature in any case less than the temperature of the first shield,
    measuring the temperature of said cell,
    controlling the heat flux between said cell and said first shield by controlling the temperature of said cell and the temperature of said first shield,
    wherein said calorimetric cell provides an introduction/extraction duct that crosses said calorimetric head at least for a part thereof, said duct and said first shield being separated by a gap, and
    wherein said introduction/extraction duct crosses said first and said second shield for all its length and comprises a central portion made of a material with high thermal conductivity and two side portions made of a material with lower thermal conductivity.

12. Method, according to claim 11, wherein said first shield is kept at a temperature equal to said calorimetric cell, whereby said heat flux between said cell and said first shield is zeroed.

13. Method according to claim 11, additionally comprising heating said second shield and monitoring said heating for keeping said second shield at a temperature lower than said first shield for a determined value.

* * * * *